United States Patent
Grover et al.

(10) Patent No.: US 10,639,113 B2
(45) Date of Patent: May 5, 2020

(54) ROBOTIC SURGICAL SYSTEMS AND INSTRUMENT DRIVE UNITS

(71) Applicant: Covidien LP, Mansfield, MA (US)

(72) Inventors: Simon R. Grover, Cambridge (GB); Charles F. Kilby, Cambridgeshire (GB); Daniel L. Fuller, Haverhill (GB)

(73) Assignee: Covidien LP, Mansfield, MA (US)

( * ) Notice: Subject to any disclaimer, the term of this patent is extended or adjusted under 35 U.S.C. 154(b) by 751 days.

(21) Appl. No.: 15/309,833

(22) PCT Filed: Apr. 28, 2015

(86) PCT No.: PCT/US2015/027871
§ 371 (c)(1),
(2) Date: Nov. 9, 2016

(87) PCT Pub. No.: WO2015/175200
PCT Pub. Date: Nov. 19, 2015

(65) Prior Publication Data
US 2017/0265951 A1    Sep. 21, 2017

Related U.S. Application Data

(60) Provisional application No. 61/992,700, filed on May 13, 2014.

(51) Int. Cl.
*A61B 34/00* (2016.01)
*A61B 34/35* (2016.01)
(Continued)

(52) U.S. Cl.
CPC ........ *A61B 34/35* (2016.02); *A61B 17/00234* (2013.01); *A61B 34/30* (2016.02);
(Continued)

(58) Field of Classification Search
CPC ......... A61B 34/35; A61B 34/30; A61B 34/71; A61B 34/74; A61B 46/10;
(Continued)

(56) References Cited

U.S. PATENT DOCUMENTS 4,314,552 A * 2/1982 Moon ................. A61G 13/009
606/242
4,974,830 A * 12/1990 Genovese ............ A61H 1/0259
601/24

(Continued)

FOREIGN PATENT DOCUMENTS

| CN | 101426412 A | 5/2009 |
| EP | 1442720 | 8/2004 |
| WO | 2009094670 A1 | 7/2009 |

OTHER PUBLICATIONS

Chinese First Office Action corresponding to counterpart Patent Application CN 201580025092.1 dated Jul. 25, 2018.
(Continued)

*Primary Examiner* — Carl H Layno
*Assistant Examiner* — Michael J Lau

(57) ABSTRACT

An instrument control unit for use with a surgical instrument, is provided. The instrument control unit comprises first and second plates, first and second lead screws, first and second yokes, and first and second motors. The first and second plates define a sleeve therebetween. Each of the first and second lead screws is disposed between the first and second plates. Each of the first and second yokes is threadedly engaged with its respective lead screw. The motors are disposed in mechanical cooperation with respective lead screws. Actuation of the motors causes rotation of its respective lead screw, which results in movement of its respective yoke along the longitudinal axis, and which is configured to effect a first function of a surgical instrument engaged with the instrument control unit.

15 Claims, 9 Drawing Sheets

(51) Int. Cl.
*A61B 46/10* (2016.01)
*A61B 34/30* (2016.01)
*A61B 17/00* (2006.01)
*A61B 17/29* (2006.01)
*A61B 90/00* (2016.01)

(52) U.S. Cl.
CPC .............. *A61B 34/71* (2016.02); *A61B 46/10* (2016.02); *A61B 34/74* (2016.02); *A61B 2017/00199* (2013.01); *A61B 2017/00225* (2013.01); *A61B 2017/00398* (2013.01); *A61B 2017/00477* (2013.01); *A61B 2017/2931* (2013.01); *A61B 2017/2943* (2013.01); *A61B 2034/742* (2016.02); *A61B 2090/064* (2016.02)

(58) Field of Classification Search
CPC ........ A61B 17/00234; A61B 2090/064; A61B 2017/00199; A61B 2017/00225; A61B 2017/00398; A61B 2017/00477; A61B 2017/2931; A61B 2017/2943; A61L 346/10
USPC ..................................................... 606/1, 130
See application file for complete search history.

(56) References Cited

U.S. PATENT DOCUMENTS

| | | | | |
|---|---|---|---|---|
| 5,156,166 A * | 10/1992 | Sebring | ................ | A61B 6/0457 378/209 |
| 5,354,158 A * | 10/1994 | Sheldon | ................ | B23Q 1/5462 248/631 |
| 5,582,617 A * | 12/1996 | Klieman | ................ | A61B 17/29 606/170 |
| 5,626,595 A * | 5/1997 | Sklar | .............. | A61B 17/320016 606/170 |
| 5,779,623 A * | 7/1998 | Bonnell | ................. | A61B 90/50 414/431 |
| 5,792,165 A * | 8/1998 | Klieman | ................ | A61B 17/29 606/170 |
| 6,330,837 B1 * | 12/2001 | Charles | .................... | B25J 11/00 74/490.06 |
| 6,665,554 B1 * | 12/2003 | Charles | .................. | A61B 90/36 600/427 |
| 2004/0024385 A1 * | 2/2004 | Stuart | .................... | B25J 9/1065 606/1 |
| 2006/0258956 A1 * | 11/2006 | Haberstich | ......... | A61B 10/0041 600/567 |
| 2008/0033284 A1 * | 2/2008 | Hauck | .................. | A61B 1/0052 600/424 |
| 2008/0058776 A1 * | 3/2008 | Jo | .......................... | A61B 34/70 606/1 |
| 2009/0264831 A1 * | 10/2009 | Thompson | .............. | A61M 5/19 604/191 |
| 2011/0060346 A1 * | 3/2011 | Jensen | ................... | B25J 9/1065 606/130 |
| 2011/0118754 A1 * | 5/2011 | Dachs, II | ............... | A61B 34/30 606/130 |
| 2011/0282356 A1 * | 11/2011 | Solomon | ................ | A61B 90/98 606/130 |
| 2012/0116416 A1 | 5/2012 | Neff et al. | | |
| 2012/0215234 A1 * | 8/2012 | Chowaniec | ........ | A61B 17/0469 606/144 |
| 2013/0060278 A1 * | 3/2013 | Bozung | .................. | A61B 34/20 606/205 |
| 2013/0325034 A1 | 12/2013 | Schena et al. | | |
| 2014/0005678 A1 * | 1/2014 | Shelton, IV | ..... | A61B 17/07207 606/130 |
| 2016/0303743 A1 | 10/2016 | Rockrohr | | |

OTHER PUBLICATIONS

International Search Report for (PCT/US2015/027871) date of completion is Jul. 28, 2015 (6 pages).

* cited by examiner

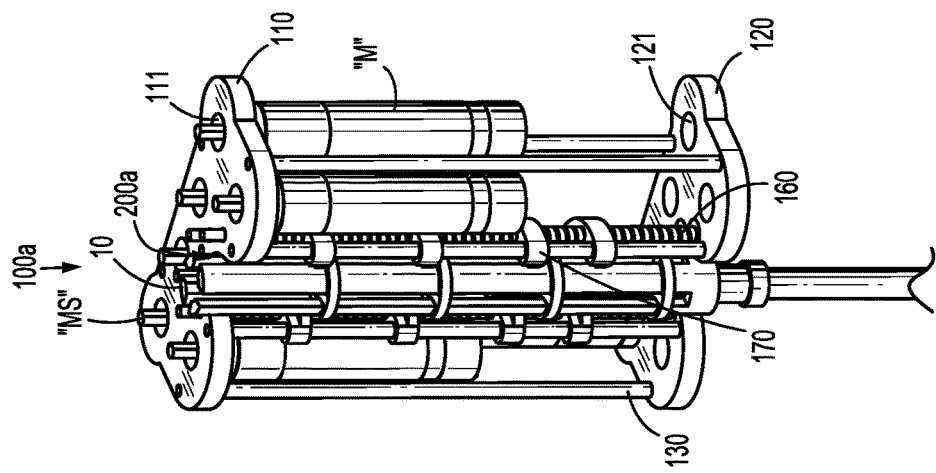
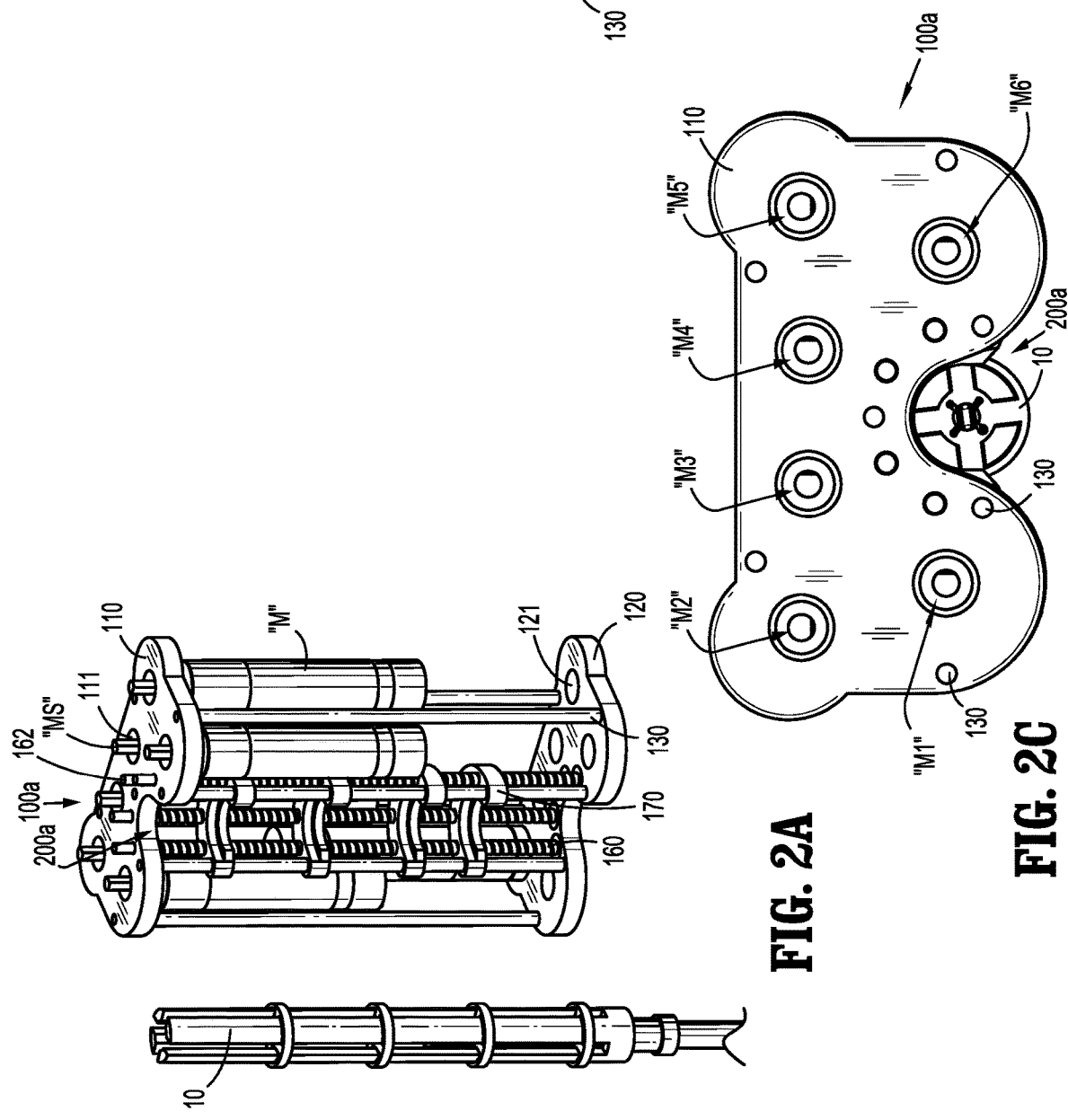

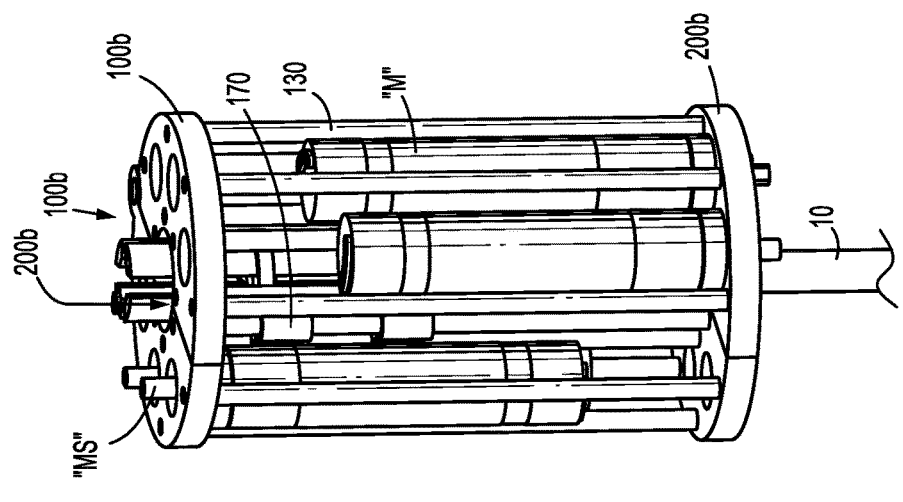
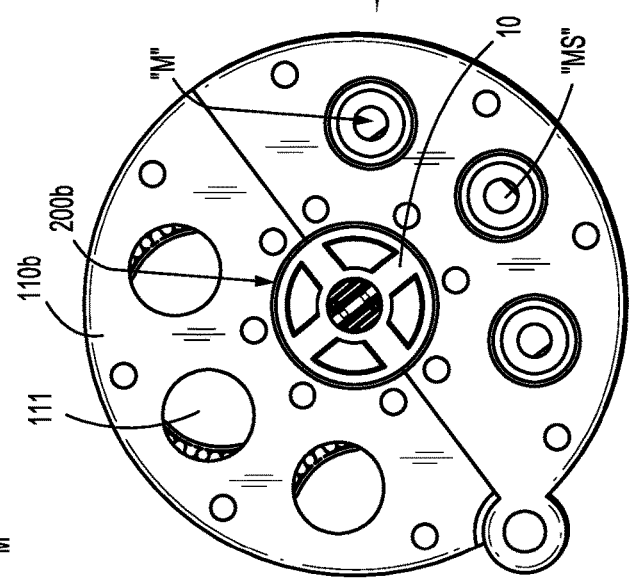
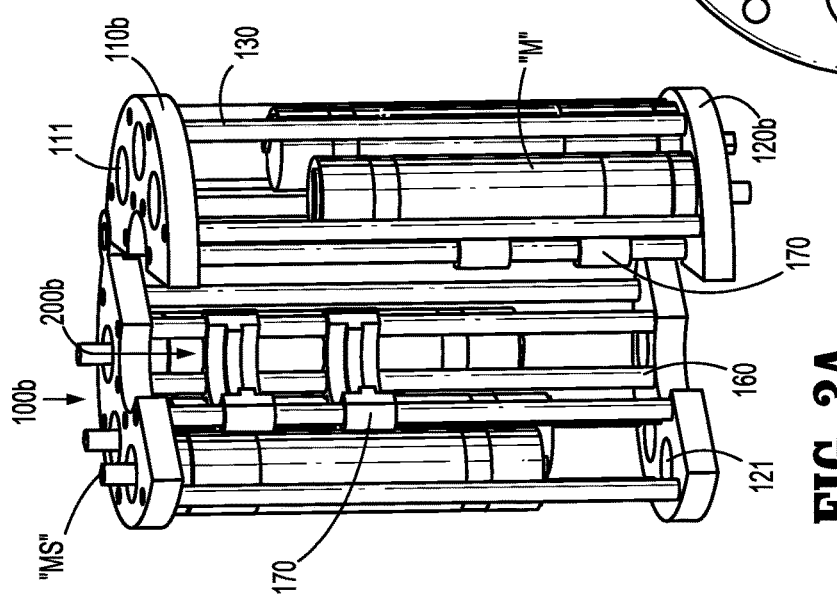
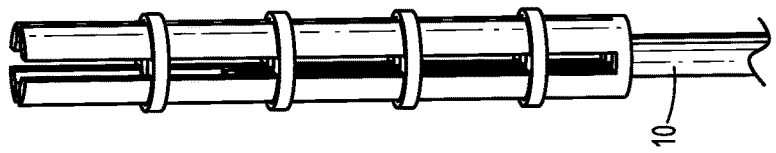

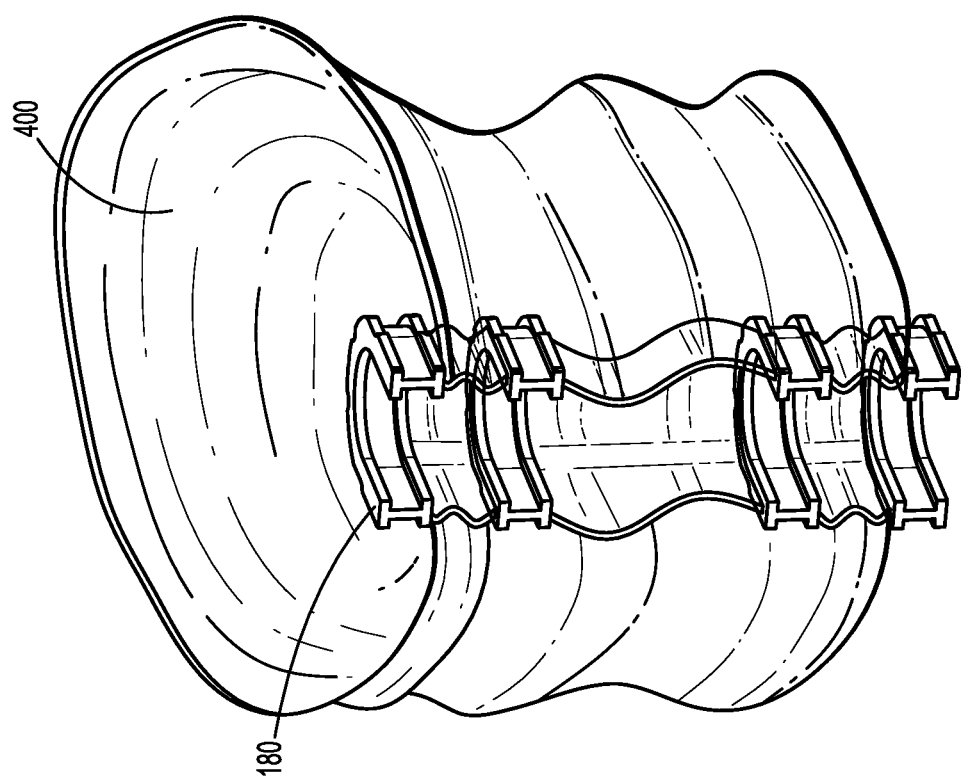

ROBOTIC SURGICAL SYSTEMS AND INSTRUMENT DRIVE UNITS

CROSS-REFERENCE TO RELATED APPLICATIONS

This application is a U.S. National Stage Application filed under 35 U.S.C. § 371(a) of International Patent Application No. PCT/US2015/027871, filed Apr. 28, 2015, which claims the benefit of and priority to U.S. Provisional Patent Application No. 61/992,700, filed May 13, 2014, the entire disclosure of which is incorporated by reference herein.

BACKGROUND

Robotic surgical systems have been used in minimally invasive medical procedures. Some robotic surgical systems include a console supporting a robot arm, and at least one end effector such as forceps or a grasping tool that is mounted to the robot arm via a wrist assembly. During a medical procedure, the end effector and the wrist assembly are inserted into a small incision (via a cannula) or a natural orifice of a patient to position the end effector at a work site within the body of the patient.

Cables extend from the robot console, through the robot arm, and connect to the wrist assembly and/or end effector. In some instances, the cables are actuated by means of motors that are controlled by a processing system including a user interface for a surgeon or clinician to be able to control the robotic surgical system including the robot arm, the wrist assembly and/or the end effector.

In some instances, the wrist assembly provides three degrees of freedom for movement of the end effector through the use of cables or cable pairs, one for each degree of freedom. For example, for grasping or cutting end effectors, the wrist assembly provides the three degrees of freedom by allowing changes to a pitch, a yaw, and an opening and closing of the end effector.

Prior to or during use of the robotic system, surgical instruments are selected and connected to instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult. Further, cables for actuating functions of the surgical instrument can become entangled upon rotation of the surgical instrument relative to the instrument drive unit.

As surgical instruments have become more versatile and complex, there is a need for the wrist assembly and an instrument drive unit associated therewith to provide additional degrees of freedom in order to more precisely control more functions of the surgical instrument. Additionally, since the wrist assembly and the instrument drive unit are often reusable, there is a need to minimize possible contamination of the instrument drive unit.

SUMMARY

The present disclosure relates to an instrument control unit for use with a surgical instrument. The instrument control unit comprises first and second plates, first and second lead screws, first and second yokes, and first and second motors. The second plate is disposed in spaced relation from the first plate. The first plate and the second plate define a sleeve therebetween. The sleeve defines a longitudinal axis and is configured to accept a surgical instrument at least partially therein. Each of the first and second lead screws is disposed between the first plate and the second plate. Each of the first and second yokes is threadedly engaged with its respective lead screw. The first motor is disposed in mechanical cooperation with the first lead screw. Actuation of the first motor causes rotation of the first lead screw, which results in movement of the first yoke along the longitudinal axis, and which is configured to effect a first function of a surgical instrument engaged with the instrument control unit. The second motor is disposed in mechanical cooperation with the second lead screw. Actuation of the second motor causes rotation of the second lead screw, which results in movement of the second yoke along the longitudinal axis, and which is configured to effect a second function of a surgical instrument engaged with the instrument control unit.

In disclosed embodiments of the present disclosure, the first plate includes an arcuate portion and the second plate includes an arcuate portion. The sleeve is defined between the arcuate portion of the first plate and the arcuate portion of the second plate.

It is envisioned that each of the first and second yokes is arcuate.

Embodiments of the instrument control unit of the present disclosure also includes third and fourth lead screws disposed between the first plate and the second plate, third and fourth yokes threadedly engaged with their respective lead screws, and third and fourth motors disposed in mechanical cooperation with respective lead screws. Actuation of the third motor causes rotation of the third lead screw, which results in movement of the third yoke along the longitudinal axis, and which is configured to effect a third function of a surgical instrument engaged with the instrument control unit. Actuation of the fourth motor causes rotation of the fourth lead screw, which results in movement of the fourth yoke along the longitudinal axis, and which is configured to effect a fourth function of a surgical instrument engaged with the instrument control unit.

It is further envisioned that the instrument control unit comprises a first interface gear and a fifth motor disposed in mechanical communication with the first interface gear. Actuation of the fifth motor results in rotation of the first interface gear, which is configured to effect a fifth function of a surgical instrument engaged with the instrument control unit. Additionally, it is disclosed that the instrument control unit comprises a second interface gear and a sixth motor disposed in mechanical communication with the second interface gear. Actuation of the sixth motor results in rotation of the second interface gear, which is configured to effect a sixth function of a surgical instrument engaged with the instrument control unit.

In disclosed embodiments, at least a majority of each of the first motor, the second motor, the third motor, and the fourth motor is disposed between the first plate and the second plate. It is further disclosed that each of the first motor, the second motor, the third motor, and the fourth motor includes a shaft that extends through at least one of the first plate and the second plate.

In embodiments of the disclosure, each of the first plate and the second plate includes two portions that are hingedly connected to each other. Here, each of the first plate and the second plate is configured to move between an open position to accept a surgical instrument at least partially within the sleeve, and a closed position to surround a diameter of a surgical instrument.

It is further disclosed that a control device is configured to remotely control actuation of the first motor and the second motor.

In disclosed embodiment, a drape is included to essentially enclose the first plate, the second plate, the first lead screw, the second lead screw, the first motor and the second motor, while permitting longitudinal movement of the first yoke and the second yoke to be transferred to a portion of a surgical instrument engaged with the instrument control unit. Additionally, it is disclosed that the instrument control unit includes a first interface collar and a second interface collar. The first interface collar is configured to mechanically engage the first yoke and a portion of a surgical instrument engaged with the instrument control unit. The second interface collar is configured to mechanically engage the second yoke and a portion of a surgical instrument engaged with the instrument control unit. The drape is secured to the first interface collar and the second interface collar.

The present disclosure also relates to a robotic surgical system comprising an instrument control unit, a control device and a surgical instrument. The instrument control unit includes first and second plates, a first lead screw, a first yoke, and a first motor. The second plate is disposed in spaced relation from the first plate. The first and second plates define a sleeve therebetween. The sleeve defines a longitudinal axis. The first lead screw is disposed between the first plate and the second plate. The first yoke is threadedly engaged with the first lead screw. The first motor is disposed in mechanical cooperation with the first lead screw such that actuation of the first motor causes rotation of the first lead screw, which results in movement of the first yoke along the longitudinal axis. The control device is disposed in communication with the instrument control unit and is configured to remotely control actuation of the first motor. The surgical instrument is configured for engagement with the instrument control unit. Movement of the first yoke along the longitudinal axis is configured to effect a first function of the surgical instrument engaged with the instrument control unit.

In disclosed embodiments, the instrument control unit also includes a second lead screw disposed between the first plate and the second plate, a second yoke threadedly engaged with the second lead screw, and a second motor disposed in mechanical cooperation with the second lead screw such that actuation of the second motor by the control device causes rotation of the second lead screw, which results in movement of the second yoke along the longitudinal axis, which is configured to effect a second function of the surgical instrument engaged with the instrument control unit. Here, it is disclosed that each of the first motor, and the second motor includes a shaft that extends through at least one of the first plate and the second plate.

In embodiments of the disclosure, a drape essentially encloses the first plate, the second plate, the first lead screw and the first motor, while permitting longitudinal movement of the first yoke to be transferred to a portion of the surgical instrument engaged with the instrument control unit. Here, it is disclosed that the instrument control unit also includes a first interface collar configured to mechanically engage the first yoke and a portion of the surgical instrument engaged with the instrument control unit. The drape is secured to the first interface collar. It is further disclosed that the surgical instrument includes a first bearing configured to mechanically engage the first interface collar.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 2A is a perspective view of an instrument drive unit in accordance with embodiments of the present disclosure;

FIG. 2B is a perspective view of the instrument drive unit of FIG. 2A shown with a surgical instrument engaged therewith;

FIG. 2C is a top view of the instrument drive unit and surgical instrument of FIG. 2B;

FIG. 3A is a perspective view of another instrument drive unit in accordance with embodiments of the present disclosure;

FIG. 3B is a perspective view of the instrument drive unit of FIG. 3A shown with a surgical instrument engaged therewith;

FIG. 3C is a top view of the instrument drive unit and the surgical instrument of FIG. 3B;

FIG. 10 is a perspective view of the interface features of FIG. 7 illustrated with a protective barrier covering the instrument drive unit of FIG. 7.

DETAILED DESCRIPTION

Figure 1B:
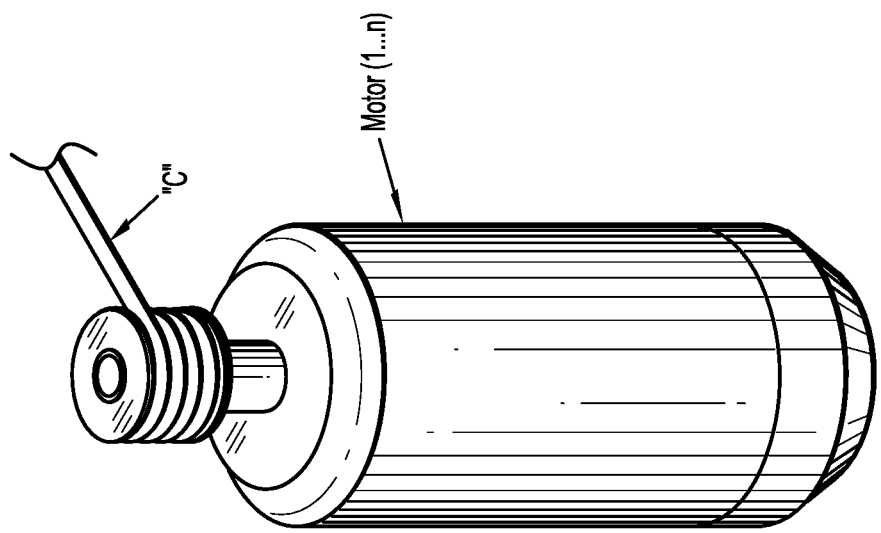
FIG. 1B is a schematic, perspective view of a motor of a control device of the medical work station of FIG. 1A.

Embodiments of the presently disclosed instrument drive units are described in detail with reference to the drawings, in which like reference numerals designate identical or corresponding elements in each of the several views. As used herein the term "distal" refers to that portion of the instrument drive unit that is farther from the user, while the term "proximal" refers to that portion of the instrument drive unit that is closer to the user.

Figure 1A:
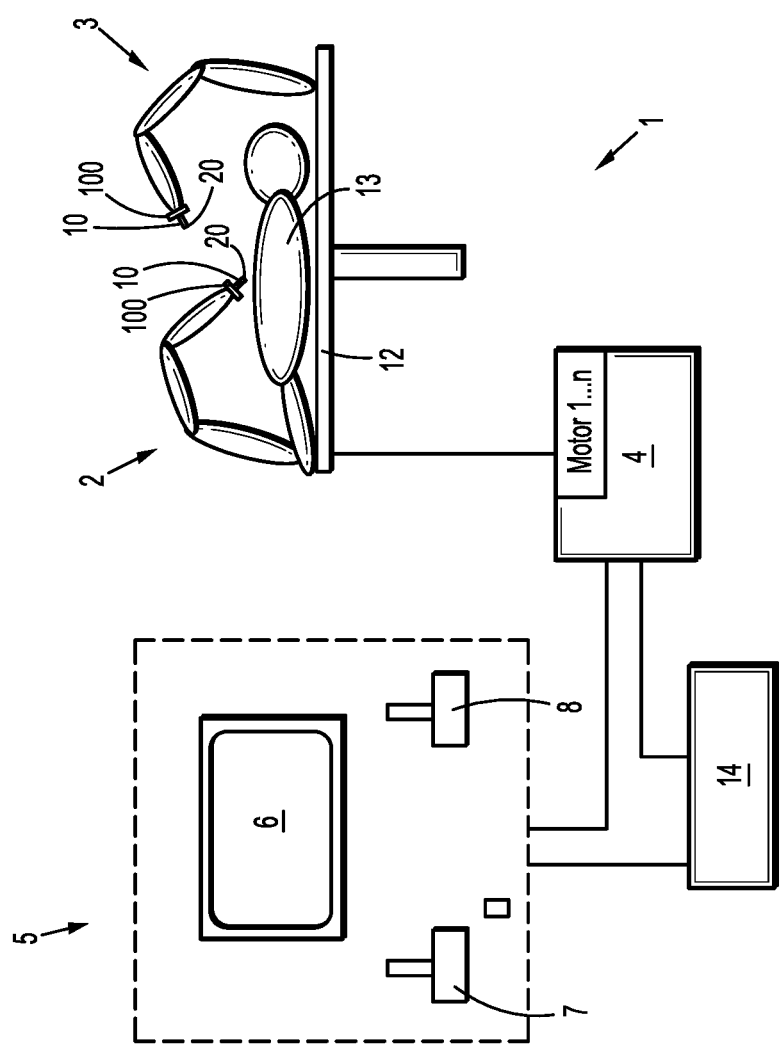
FIG. 1A is a schematic illustration of a medical work station and operating console in accordance with the present disclosure.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an instrument drive unit 100, to which may be attached, for example, a surgical instrument 10 supporting an end effector 20, in accordance with any one of several embodiments of instrument drive units 100 disclosed herein, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, instrument drive units 100, and thus the surgical instruments 10 execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of surgical instrument 10. Medical work station 1 may also include more than two robot arms 2, 3, the additional robot arms likewise being connected to control device 4 and being telemanipulatable by means of operating console 5. An instrument control unit and a surgical instrument may also be attached to the additional robot arm. Medical work station 1 may include a database 14, in particular coupled to with control device 4, in which are stored for example pre-operative data from patient 13 and/or anatomical atlases.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Control device 4 may control a plurality of motors (e.g., "M1"-"M6"). Motors may be part of instrument control unit 100 and/or disposed externally of instrument control unit 100. For example, it is envisioned that motors "M1"-"M5" are located within instrument control unit 100 (see FIGS. 4-9) and that motor "M6" is located externally of instrument control unit 100. It is further envisioned that six motors "M1"-"M6" are located within instrument control unit (see FIGS. 2A-3C). Other combinations of motors "M" being within or located externally of instrument control unit 100 are also contemplated. Motors "M" (e.g., motors "M" being located externally of instrument control unit 100) may be configured to wind-up or let out a length of a cable "C" (FIG. 1B) extending through a robot arm to instrument control unit 100, and/or to drive a gear of instrument control unit 100. In use, as motors "M" are driven, the movement of cables "C" and gears effect operation and/or movement of surgical instrument 10, as discussed below. It is contemplated that control device 4 coordinates the activation of the various motors (Motor 1 . . . n) to coordinate an operation and/or movement of surgical instrument 10. Although FIG. 1B shows a single cable "C" that is wound up or let out by a single motor, in some instances two or more cables or two ends of a single cable may be wound up or let out by a single motor. For example, in some instances, two cables or cable ends may be coupled in opposite directions to a single motor so that as the motor is activated in a first direction, one of the cables winds up while the other cable lets out. Other cable and gear configurations may be used in different embodiments to control various movement of surgical instrument 10 and end effector 20. It is envisioned that each motor corresponds to a separate degree of freedom of surgical instrument 10 engaged with instrument control unit 100. Reference may be made to commonly owned U.S. Provisional Patent Application No. 61/914,632, filed on Dec. 11, 2013, entitled "Wrist and Jaw Assemblies for Robotic Surgical Systems," the entire content of which is incorporated herein by reference, for a detailed discussion of illustrative examples of the construction and operation of end effectors 20 for use with instrument control unit 100.

Turning now to FIGS. 2A-9, instrument control units for connection to robot arms 2, 3 and for manipulation by control device 4, are generally designated as 100a (FIGS. 2A-2C), 100b (FIGS. 3A-3C) and 100c (e.g., FIG. 4), and are collectively referred to herein as instrument control unit 100. Additionally, for ease of description, common or related features from instrument control units 100a, 100b, and 100c will be referred to by the same reference number.

In each of the embodiments, instrument control unit 100 includes a first plate 110, a second plate 120, a plurality of connectors 130, a plurality of motors "M," a plurality of gears 140, 150 (see FIG. 4), a plurality of lead screws 160, and a plurality of yokes 170. An arcuate sleeve 200 is defined between arcuate portions of first plate 110 and second plate 120, is configured to releasably accept surgical instrument 10 therein, and defines a longitudinal axis "X-X." In the embodiments shown in FIGS. 2A-2C and 4-9, instrument control units 100a and 100c are designed to partially surround surgical instrument 10 inserted in arcuate sleeve 200a, 200c (see FIGS. 2B and 8). In the embodiment shown in FIGS. 3A-3C, instrument control unit 100b is designed to completely surround surgical instrument 10 inserted into arcuate sleeve 200b. That is, first plate 110b and second plate 120b of instrument control unit 100b each include two portions that are hingedly connected to each other, thus enabling instrument control unit 100b is move between an open position (FIG. 3A) and a closed position (FIGS. 3B and 3C) to surround a diameter of surgical instrument 10.

Connectors 130 extend between and interconnect first plate 110 and second plate 120. Each motor "M" includes a shaft "MS" that extends through an opening 111 in first plate 110 or an opening 121 in second plate 120 (see instrument control unit 100b of FIGS. 3A-3C), and is mechanically engaged with and configured to rotate a first or motor gear 140. Each motor gear 140 mechanically engages a second or lead screw gear 150. Each lead screw gear 150 is coupled to an upper portion 162 of lead screw 160; upper portion 162 of lead screw 160 extends through an opening (not shown) in first plate 110. Each lead screw 160 extends between first plate 110 and second plate 120. Each yoke 170 is threadedly engaged with a single lead screw 160, and is configured to longitudinally slide with respect to the other lead screws 160 and with respect to connectors 130 extending therethrough. For example, and with particular reference to FIG. 4, it is envisioned that a first motor "M1" mechanically engages a first motor gear 140a; first motor gear 140a mechanically engages a first lead screw gear 150a; first lead screw gear 150a is coupled to a first lead screw 160a; and first lead screw 160a is threadedly coupled to a first yoke 170a. With additional regard to yokes 170, in the illustrated embodiments each yoke 170 is arcuate and includes seven openings extending therethrough. A first opening 171 is threaded and engaged with a single lead screw 160 (e.g., first lead screw 160a). The remaining six openings 172 are configured to slidably engage the remaining three lead screws (e.g., a second lead screw 160b, a third lead screw 160c and a fourth lead screw 160d), and each of the three connectors 130. That is, the remaining openings 172 have a larger dimension than the outer dimensions of the remaining lead screws 160b, 160c, 160d and connectors 130, thus permitting the slidable relationship therebetween.

Figure 4:
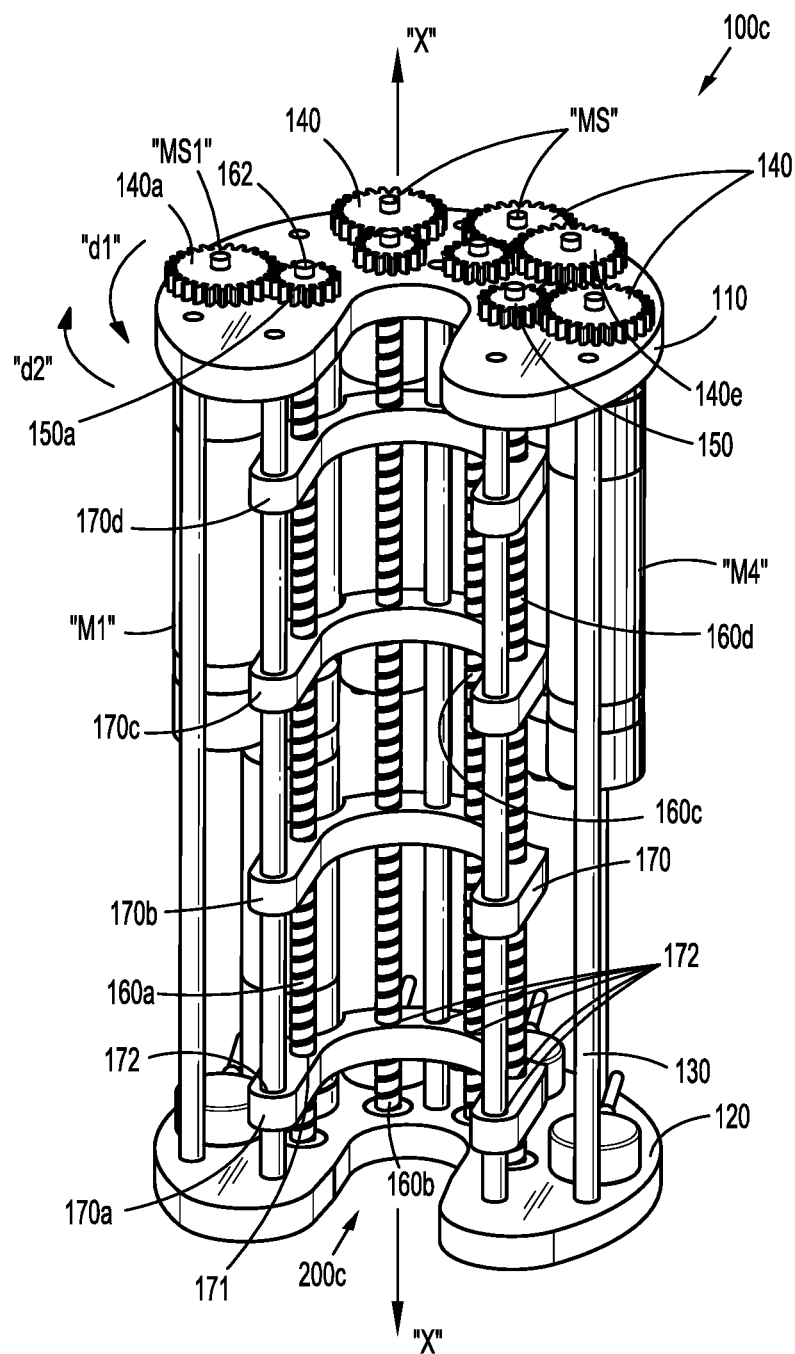
FIG. 4 is a perspective view of the instrument drive unit of FIGS. 2A-2C including a plurality of gears thereon.
Figure 5:
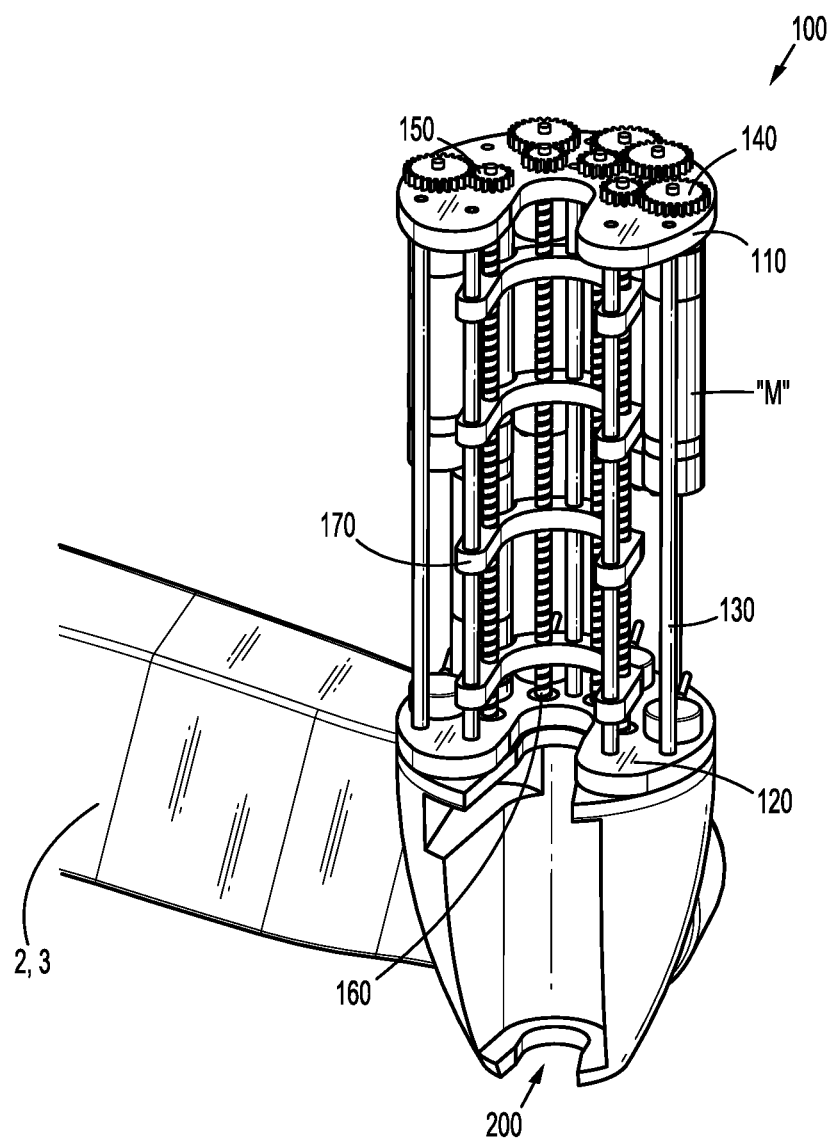
FIG. 5 is a perspective view of the instrument drive unit of FIG. 4 engaged with a robotic arm of a medical work station.

In use, each motor "M" may receive a signal from control device 4, as discussed above, to rotate in a first direction or a second direction, to control a function of surgical instrument 10. With particular reference to FIG. 4, upon receiving an appropriate signal, first motor "M1" and thus first motor shaft "MS1" rotate in a first direction (e.g., "d1"). Rotation of first motor shaft "MS1" causes a corresponding rotation of first motor gear 140a in the first direction "d1." Rotation of first motor gear 140a in the first direction "d1" results in a corresponding rotation of first lead screw gear 150a in a second direction "d2," which is opposite of the first direction "d1." Rotation of first lead screw gear 150a in the second direction "d2" causes a corresponding rotation of first lead screw 160a in the same, second direction "d2." Rotation of first lead screw 160a causes longitudinal movement (i.e., toward first plate 110 or second plate 120) of first yoke 170a along first lead screw 160a.

It is envisioned that lead screws 160 are designed to allow only a certain amount of longitudinal movement of corresponding yokes 170 (e.g., between about 0.25 inches and about 1.0 inches). It is further envisioned that the pitch of the thread on at least one lead screw 160 can be designed for coarse or fine movement of the corresponding yoke 170. Further, each lead screw 160 can include a thread with varying pitch to allow for both coarse and fine movement of the corresponding yoke 170.

Figure 7:
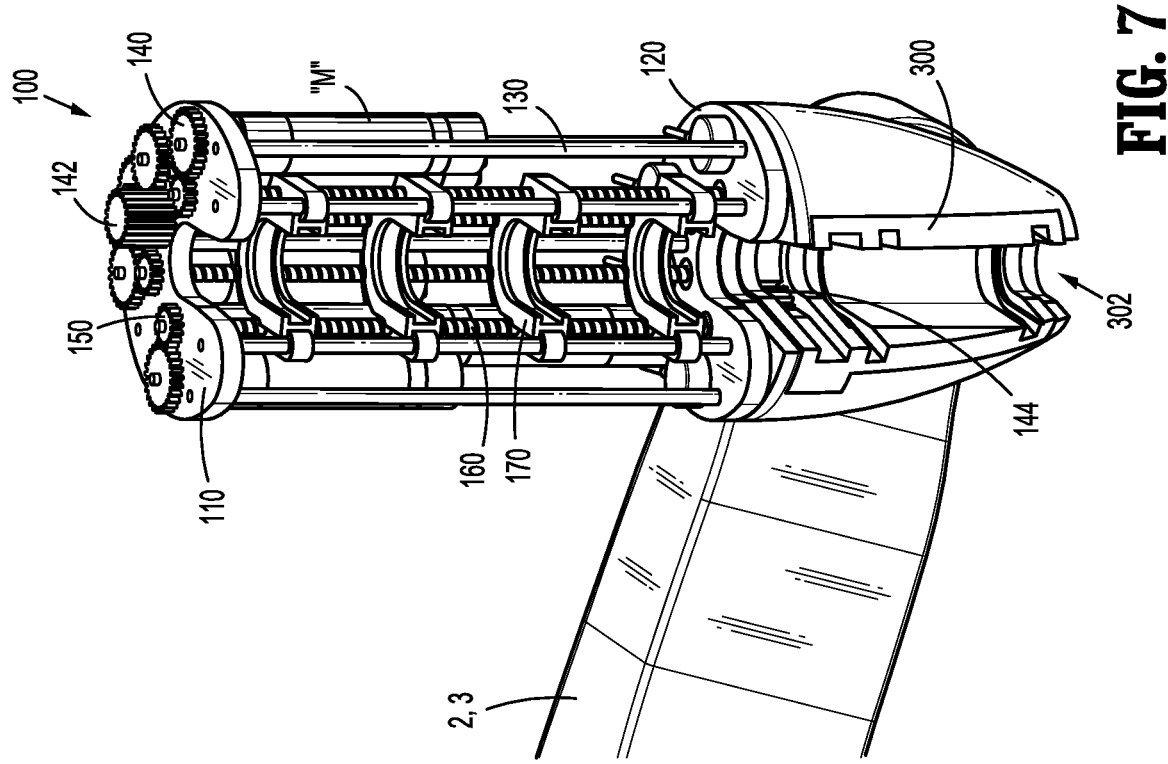
FIG. 7 is a perspective view of the instrument drive unit of FIGS. 4 and 5 engaged with the interface features of FIG. 6.
Figure 6:
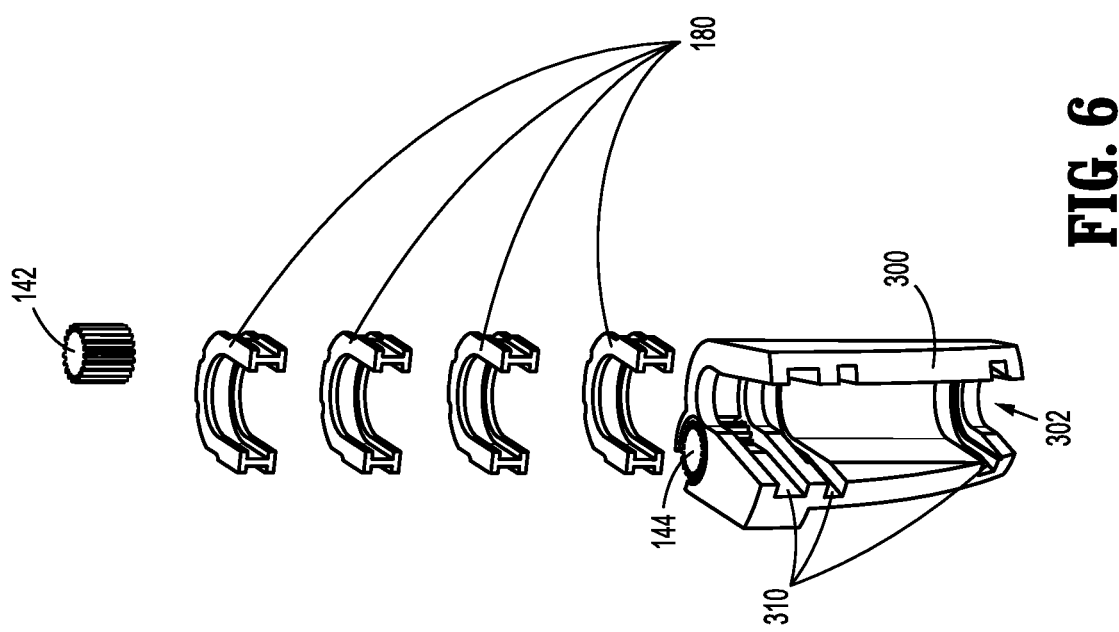
FIG. 6 is a perspective view of a plurality of interface features configured to engage the instrument drive unit of FIGS. 4 and 5 and to engage the surgical instrument.
Figure 11:
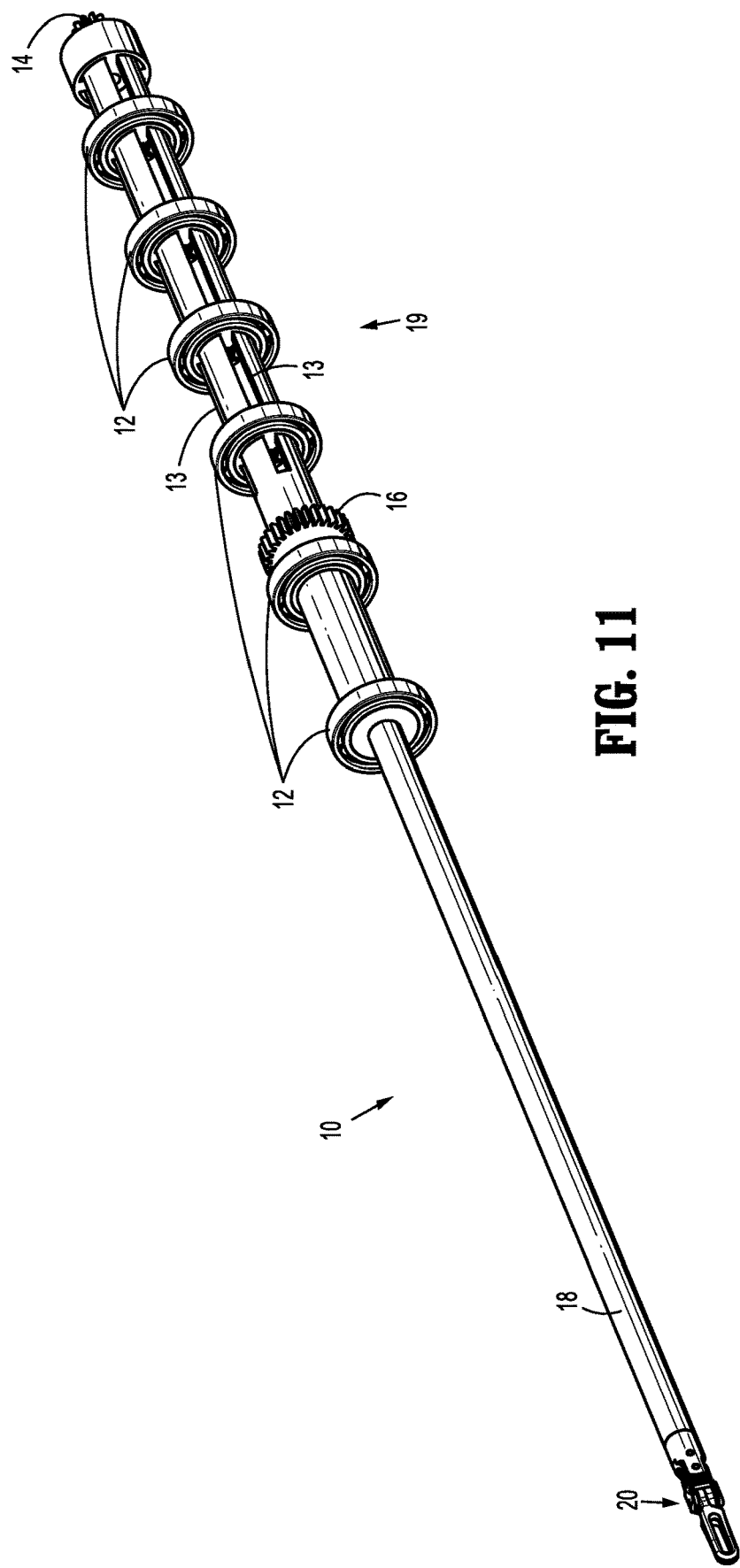
FIG. 11 is a perspective view of the surgical instrument usable with the instrument drive units of the present disclosure.

With particular reference to FIGS. 6 and 7, instrument control unit 100 also includes a plurality of collars or interface collars 180. Each collar 180 is configured to engage a single yoke 170 (e.g., via a snap-fit connection, weld, etc.) of instrument control unit 100 and is configured to engage (e.g., via a snap-fit connection) a portion (e.g., a bearing 12; see FIG. 11) of surgical instrument 10 to facilitate releasable attachment between surgical instrument 10 and instrument control unit 100. Accordingly, longitudinal movement of yokes 170, cause a corresponding longitudinal movement of the respective collars 180 and bearings 12. As shown in FIG. 11, surgical instrument 10 includes longitudinal slots 13 to accommodate longitudinal translation of bearings 12. As can be appreciated by one skilled in the art, it is envisioned that each bearing 12 is mechanically engaged with at least one element (e.g., rod, cable, etc.) of surgical instrument 10, and that longitudinal movement of the bearing 12 causes a corresponding translation of the element(s) to effect a function of the surgical instrument (e.g., approximation of the jaw members of end effector 20, articulation of the jaw members of end effector 20, firing fasteners from one jaw member toward the other, advancing a cutting member to sever tissue between the jaw members, etc.).

Thus, as can be appreciated the rotation of motors "M1"-"M4" can effect the longitudinal movement of yokes 170a-170d, and thus the longitudinal movement of bearings 12 to control four features of surgical instrument—1) approximation (opening and closing) of the jaw members; 2) articulation of the jaw members in opposite directions; 3) firing fasteners from a jaw member; and 4) advancing and retracting a cutting member.

Figure 9:
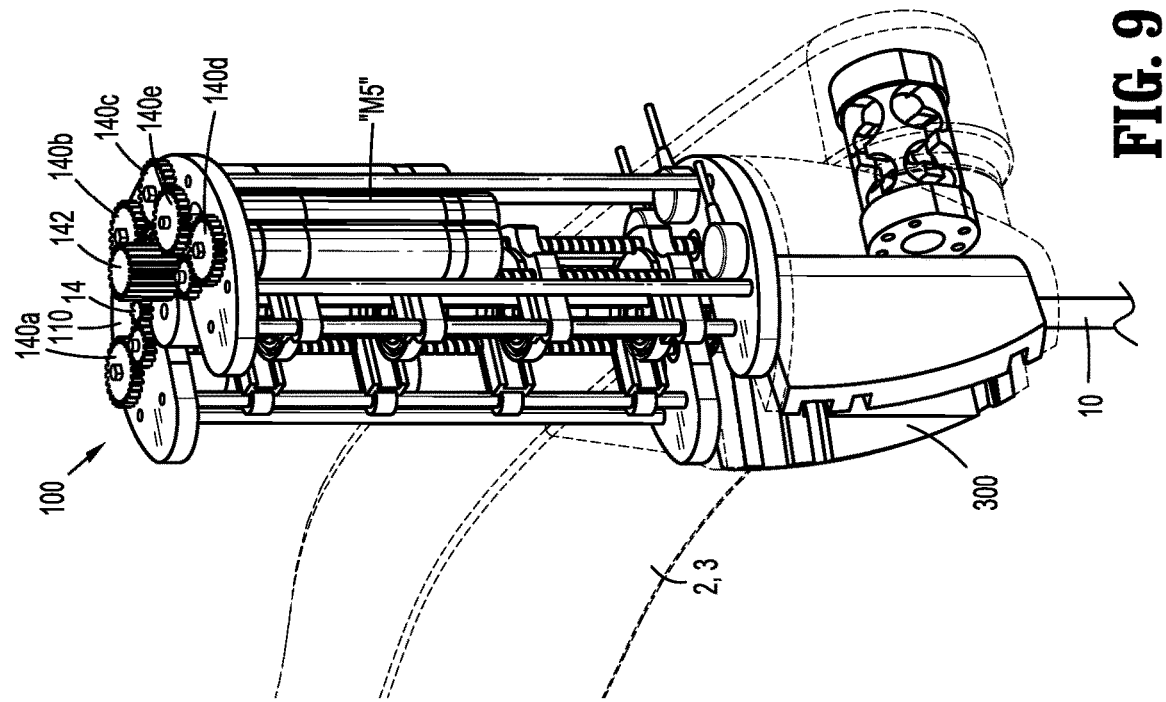
FIGS. 8 and 9 are perspective views of the instrument drive unit and the interface features of FIG. 7 engaged with the surgical instrument.
Figure 8:
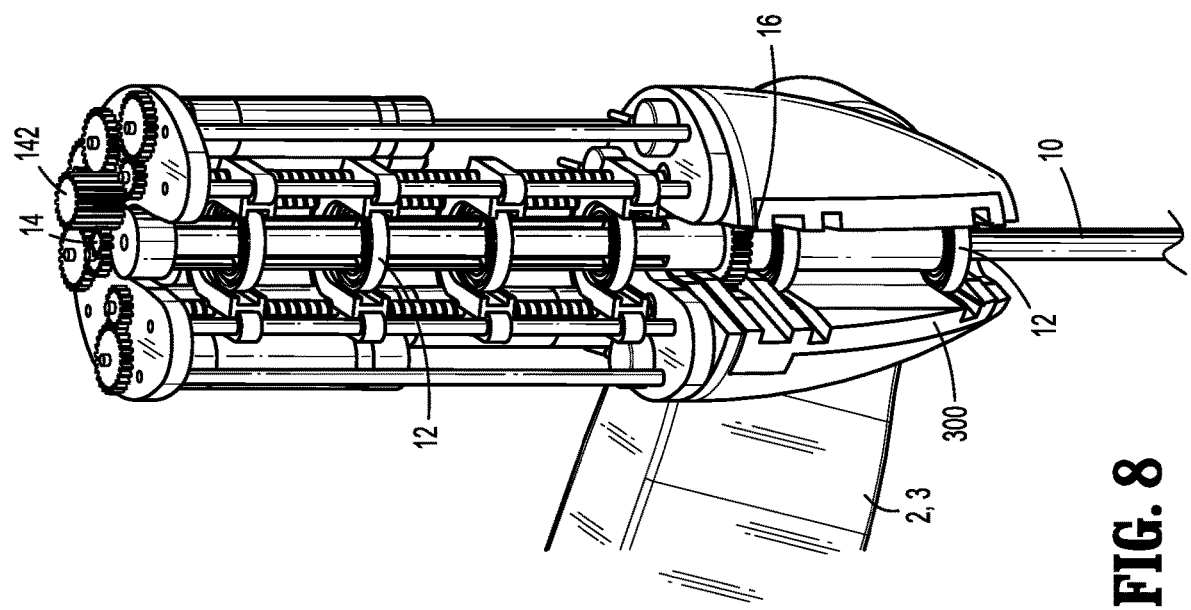

Additionally, instrument control unit 100 includes a fifth motor "M5" (see FIG. 9). Fifth motor "M5" includes a fifth motor shaft (not shown) that extends through first plate 110 and engages a fifth motor gear 140e. It is envisioned that fifth motor gear 140e is located on a different plane (i.e., farther above first plate 110) than motor gears 140a-140d, e.g., to allow instrument control unit 100c to include a smaller profile. With reference to FIGS. 6-9, instrument control unit 100 includes a first interface gear 142 configured to engage fifth motor gear 140e. First interface gear 142 is supported above first plate 110 (e.g., is rotatable about a pin extending upwards therefrom). Additionally, first interface gear 142 is configured to engage a first instrument gear 14 of surgical instrument 10 when surgical instrument 10 is engaged with instrument control unit 100 (see FIG. 8). Here, rotation of first instrument gear 14 causes rotation of end effector 20 and/or an elongated portion 18 of surgical instrument 10 with respect to a proximal portion 19 of surgical instrument 10. That is, rotation of fifth motor "M5" causes a corresponding rotation of fifth motor gear 140e, which causes a corresponding rotation of first interface gear 142, which causes a corresponding rotation of first instrument gear 14, and thus a rotation of end effector 20 and/or elongated portion 18 with respect to proximal portion 19 of surgical instrument 10.

Further, instrument control unit 100 includes a second interface gear 144 (see FIGS. 6 and 7) configured to be driven by a sixth motor "M6" (see FIGS. 2A-3C). In the embodiments of instrument control unit 100a and 100b illustrated in FIGS. 2A-2C, sixth motor "M6" includes a sixth motor shaft that extends through first plate 110 (FIGS. 2A-2C) or second plate 120 (FIGS. 3A-3C) and engages a sixth motor gear (not shown) and second interface gear 144 (not shown in FIGS. 2A-3C). Second interface gear 144 (shown in FIGS. 6 and 7) is configured to engage a second instrument gear 16 (see FIGS. 8 and 11) of surgical instrument 10 when surgical instrument 10 is engaged with control unit 100. Rotation of second instrument gear 16 causes rotation of the entire surgical instrument 10 with respect to instrument control unit 100. That is, rotation of sixth motor "M6" optionally causes a corresponding rotation of the sixth motor gear, and causes a corresponding rotation of second interface gear 144, which causes a corresponding rotation of second instrument gear 16, and thus a rotation of surgical instrument 10 within arcuate sleeve 200 of instrument control unit 100.

It is envisioned that at least one motor (e.g., sixth motor "M6") engages instrument control unit 100 via at least one cable "C" (i.e., the motor is not disposed within instrument control unit 100). Such embodiments were described above with regard to FIGS. 1A and 1B. It is further envisioned that at least one motor "M" receives signals wirelessly (e.g., from control device 4).

With reference to FIGS. 6-9, an interface housing 300 is illustrated. Interface housing 300 is supported below second plate 120 of instrument control unit 100 and is configured to engage a robot arm 2 or 3, and is configured to releasably accept a portion of surgical instrument 10 in an arcuate sleeve 302 defined therein. Arcuate sleeve 302 of interface housing 300 is longitudinally aligned with arcuate sleeve 200 of instrument control unit 100. In the embodiment illustrated in FIG. 6, interface housing 300 rotatably supports second interface gear 144 at least partially therein. Further, interface housing 300 includes a plurality of grooves 310 therein. Grooves 310 are configured to releasably accept bearings 12 of surgical instrument 10 therein. When engaged, bearings 12 of surgical instrument 10 are rotatable with respect to the respective grooves 310. The interaction between bearings 12 and grooves 310 allows surgical instrument 10 to rotate with respect to interface housing 300, while preventing longitudinal translation of surgical instrument 10 with respect to interface housing 300.

Additionally, interface housing 300 helps provide a sterile barrier between surgical instrument 10 and robot arm 2, 3.

It is further envisioned that instrument control unit 100 includes a plurality of load cells 210 thereon (see FIGS. 4, 5 and 7-9). In a contemplated embodiment, there is a provided a load cell 210 in communication with each lead screw 160 for determining the tension of cables within surgical instrument 10 by measuring the thrust on the associated lead screw 160. Additionally, and with particular reference to FIG. 9, a torque sensor 220 may be included on a portion of robot arm 2, 3 (e.g., where instrument control unit 100 pivots with respect to robot arm 2, 3). Torque sensor 220 is configured to monitor the current of a motor (e.g., "M6") associated with rotations of surgical instrument 10.

With reference to FIG. 10, a drape 400 is shown covering or essentially enclosing instrument drive unit 100. Drape acts as a sterile barrier and is configured to prevent contamination of instrument drive unit 100 (e.g., from surgical instrument 10, bodily fluids, ambient environment, etc.) during use. It is envisioned that drape 400 is secured to interface collars 180 (e.g., via welding, gluing, etc.). Additionally, drape 400 will be flexible enough, or be secured to collars 180 with enough slack to allow for collars 180 to move in a full range of longitudinal movement (e.g., uninhibited longitudinal movement).

With regard to interface gears 142 and 144, it is envisioned that each interface gear 142, 144 includes a sterile portion (shown in FIGS. 6 and 7) which is configured to be occluded by drape 400, and a non-sterile portion (not explicitly shown) which is configured to be exposed to surgical instrument 10, and thus bodily fluids. In such embodiments, it is disclosed that a shaft interconnects the sterile portion of interface gear 142 and the non-sterile portion of interface gear 142, and that a separate shaft interconnects the sterile portion of interface gear 144 and the non-sterile portion of interface gear 144. In these embodiments, the sterile portion of each interface gear 142, 144 is similarly keyed to the respective shaft as the non-sterile portion of the respective interface gear 142, 144, such that rotation of the sterile portions causes a corresponding rotation of the respective non-sterile portions.

The present disclosure also includes a robotic surgical system including instrument drive unit 100, surgical instrument 10 and control device 4, for example, as described above. Additionally, the present disclosure includes methods of controlling a surgical instrument 10 including the use of instrument control unit 100, and methods of performing a surgical task using instrument control unit 100.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument control unit for use with a surgical instrument, the instrument control unit comprising:
    a first plate;
    a second plate disposed in spaced relation from the first plate, the first plate and the second plate defining a sleeve therebetween, the sleeve configured to accept a surgical instrument at least partially therein, the sleeve defining a longitudinal axis;
    a first lead screw disposed between the first plate and the second plate;
    a second lead screw disposed between the first plate and the second plate;
    a first yoke threadedly engaged with the first lead screw;
    a second yoke threadedly engaged with the second lead screw;
    a first motor disposed in mechanical cooperation with the first lead screw such that actuation of the first motor causes rotation of the first lead screw, which results in movement of the first yoke along the longitudinal axis, and wherein movement of the first yoke along the longitudinal axis is configured to effect a first function of a surgical instrument engaged with the instrument control unit;
    a second motor disposed in mechanical cooperation with the second lead screw such that actuation of the second motor causes rotation of the second lead screw, which results in movement of the second yoke along the longitudinal axis, and wherein movement of the second yoke along the longitudinal axis is configured to effect a second function of a surgical instrument engaged with the instrument control unit; and
    a control device configured to remotely control actuation of the first motor and the second motor.

2. The instrument control unit according to claim 1, wherein the first plate includes an arcuate portion and the second plate includes an arcuate portion, wherein the sleeve is defined between the arcuate portion of the first plate and the arcuate portion of the second plate.

3. The instrument control unit according to claim 1, wherein each of the first yoke and the second yoke is arcuate.

4. The instrument control unit according to claim 1, further comprising a third lead screw disposed between the first plate and the second plate, a third yoke threadedly engaged with the third lead screw, and a third motor disposed in mechanical cooperation with the third lead screw such that actuation of the third motor causes rotation of the third lead screw, which results in movement of the third yoke along the longitudinal axis, and wherein movement of the third yoke along the longitudinal axis is configured to effect a third function of a surgical instrument engaged with the instrument control unit.

5. The instrument control unit according to claim 4, further comprising a fourth lead screw disposed between the first plate and the second plate, a fourth yoke threadedly engaged with the fourth lead screw, and a fourth motor disposed in mechanical cooperation with the fourth lead screw such that actuation of the fourth motor causes rotation of the fourth lead screw, which results in movement of the fourth yoke along the longitudinal axis, and wherein movement of the fourth yoke along the longitudinal axis is configured to effect a fourth function of a surgical instrument engaged with the instrument control unit.

6. The instrument control unit according to claim 5, further comprising a first interface gear and a fifth motor disposed in mechanical communication with the first interface gear, wherein actuation of the fifth motor results in rotation of the first interface gear, which is configured to effect a fifth function of a surgical instrument engaged with the instrument control unit.

7. The instrument control unit according to claim 6, further comprising a second interface gear and a sixth motor disposed in mechanical communication with the second interface gear, wherein actuation of the sixth motor results in rotation of the second interface gear, which is configured to effect a sixth function of a surgical instrument engaged with the instrument control unit.

8. The instrument control unit according to claim 5, wherein at least a majority of each of the first motor, the second motor, the third motor, and the fourth motor is disposed between the first plate and the second plate.

9. The instrument control unit according to claim 5, wherein each of the first motor, the second motor, the third motor, and the fourth motor includes a shaft that extends through at least one of the first plate and the second plate.

10. The instrument control unit according to claim 1, wherein each of the first plate and the second plate includes two portions that are hingedly connected to each other, and wherein each of the first plate and the second plate is configured to move between an open position to accept a surgical instrument at least partially within the sleeve, and a closed position to surround a diameter of a surgical instrument.

11. The instrument control unit of claim 1, further comprising a drape essentially enclosing the first plate, the second plate, the first lead screw, the second lead screw, the first motor and the second motor, while permitting longitudinal movement of the first yoke and the second yoke to be transferred to a portion of a surgical instrument engaged with the instrument control unit.

12. The instrument control unit of claim 11, further comprising a first interface collar and a second interface collar, the first interface collar configured to mechanically engage the first yoke and a portion of a surgical instrument engaged with the instrument control unit, the second interface collar configured to mechanically engage the second yoke and a portion of a surgical instrument engaged with the instrument control unit, and wherein the drape is secured to the first interface collar and the second interface collar.

13. An instrument control unit for use with a surgical instrument, the instrument control unit comprising:
 a first plate;
 a second plate disposed in spaced relation from the first plate, the first plate and the second plate defining a sleeve therebetween, the sleeve configured to accept a surgical instrument at least partially therein, the sleeve defining a longitudinal axis;
 a first lead screw disposed between the first plate and the second plate;
 a second lead screw disposed between the first plate and the second plate;
 a third lead screw disposed between the first plate and the second plate;
 a first yoke threadedly engaged with the first lead screw;
 a second yoke threadedly engaged with the second lead screw;
 a third yoke threadedly engaged with the third lead screw;
 a first motor disposed in mechanical cooperation with the first lead screw such that actuation of the first motor causes rotation of the first lead screw, which results in movement of the first yoke along the longitudinal axis, and wherein movement of the first yoke along the longitudinal axis is configured to effect a first function of a surgical instrument engaged with the instrument control unit;
 a second motor disposed in mechanical cooperation with the second lead screw such that actuation of the second motor causes rotation of the second lead screw, which results in movement of the second yoke along the longitudinal axis, and wherein movement of the second yoke along the longitudinal axis is configured to effect a second function of a surgical instrument engaged with the instrument control unit; and
 a third motor disposed in mechanical cooperation with the third lead screw such that actuation of the third motor causes rotation of the third lead screw, which results in movement of the third yoke along the longitudinal axis, and wherein movement of the third yoke along the longitudinal axis is configured to effect a third function of a surgical instrument engaged with the instrument control unit.

14. An instrument control unit for use with a surgical instrument, the instrument control unit comprising:
 a first plate;
 a second plate disposed in spaced relation from the first plate, the first plate and the second plate defining a sleeve therebetween, the sleeve configured to accept a surgical instrument at least partially therein, the sleeve defining a longitudinal axis, each of the first plate and the second plate includes two portions that are hingedly connected to each other, and each of the first plate and the second plate is configured to move between an open position to accept a surgical instrument at least partially within the sleeve, and a closed position to surround a diameter of a surgical instrument;
 a first lead screw disposed between the first plate and the second plate;
 a second lead screw disposed between the first plate and the second plate;
 a first yoke threadedly engaged with the first lead screw;
 a second yoke threadedly engaged with the second lead screw;
 a first motor disposed in mechanical cooperation with the first lead screw such that actuation of the first motor causes rotation of the first lead screw, which results in movement of the first yoke along the longitudinal axis, and wherein movement of the first yoke along the longitudinal axis is configured to effect a first function of a surgical instrument engaged with the instrument control unit; and
 a second motor disposed in mechanical cooperation with the second lead screw such that actuation of the second motor causes rotation of the second lead screw, which results in movement of the second yoke along the longitudinal axis, and wherein movement of the second yoke along the longitudinal axis is configured to effect a second function of a surgical instrument engaged with the instrument control unit.

15. An instrument control unit for use with a surgical instrument, the instrument control unit comprising:
 a first plate;
 a second plate disposed in spaced relation from the first plate, the first plate and the second plate defining a sleeve therebetween, the sleeve configured to accept a surgical instrument at least partially therein, the sleeve defining a longitudinal axis;
 a first lead screw disposed between the first plate and the second plate;
 a second lead screw disposed between the first plate and the second plate;
 a first yoke threadedly engaged with the first lead screw;
 a second yoke threadedly engaged with the second lead screw;
 a first motor disposed in mechanical cooperation with the first lead screw such that actuation of the first motor causes rotation of the first lead screw, which results in movement of the first yoke along the longitudinal axis, and wherein movement of the first yoke along the longitudinal axis is configured to effect a first function of a surgical instrument engaged with the instrument control unit;
 a second motor disposed in mechanical cooperation with the second lead screw such that actuation of the second motor causes rotation of the second lead screw, which results in movement of the second yoke along the longitudinal axis, and wherein movement of the second yoke along the longitudinal axis is configured to effect a second function of a surgical instrument engaged with the instrument control unit; and a drape essentially enclosing the first plate, the second plate, the first lead screw, the second lead screw, the first motor, and the second motor, while permitting longitudinal movement of the first yoke and the second yoke to be transferred to a portion of a surgical instrument engaged with the instrument control unit.

\* \* \* \* \*